United States Patent [19]

Hollister

[11] Patent Number: 5,154,285
[45] Date of Patent: Oct. 13, 1992

[54] NEEDLE ASSEMBLY HOLDER WITH ROTATABLE SAFETY SHEATH MEMBER

[75] Inventor: William H. Hollister, Nelson, N.H.

[73] Assignee: Smiths Industries Medical Systems, Inc., Keene, N.H.

[21] Appl. No.: 811,298

[22] Filed: Dec. 20, 1991

[51] Int. Cl.$^5$ .......................... A61M 5/32; A61M 5/00
[52] U.S. Cl. ...................................... 206/365; 604/192
[58] Field of Search ........................ 206/365; 604/192

[56] References Cited

U.S. PATENT DOCUMENTS

| | | |
|---|---|---|
| 1,779,451 | 10/1930 | Sponsel . |
| 2,700,385 | 1/1955 | Ortiz . |
| 2,836,942 | 6/1958 | Miskel . |
| 2,854,976 | 10/1958 | Heydrich . |
| 2,953,243 | 9/1960 | Roehr . |
| 3,021,942 | 2/1962 | Hamilton . |
| 3,073,307 | 1/1963 | Stevens . |
| 3,074,542 | 1/1963 | Myerson et al. . |
| 3,255,873 | 6/1966 | Speelman . |
| 3,294,231 | 12/1966 | Vanderbeck . |
| 3,323,523 | 6/1967 | Scislowicz et al. . |
| 3,329,146 | 7/1967 | Waldman, Jr. . |
| 3,333,682 | 8/1967 | Burke . |
| 3,342,319 | 9/1967 | Faulseit .............................. 206/365 |
| 3,367,488 | 2/1968 | Hamilton . |
| 3,485,239 | 12/1969 | Vanderbeck . |
| 3,537,452 | 11/1970 | Wilks . |
| 3,610,240 | 10/1971 | Harautuneian . |
| 3,658,061 | 4/1972 | Hall . |
| 3,828,775 | 8/1974 | Armel . |
| 3,890,971 | 6/1975 | Leeson et al. . |
| 3,904,033 | 9/1975 | Haerr . |
| 3,934,722 | 1/1976 | Goldberg . |
| 3,968,876 | 7/1976 | Brookfield . |
| 4,113,090 | 9/1978 | Carstens . |
| 4,139,009 | 2/1979 | Alvarez . |
| 4,175,008 | 11/1979 | White . |
| 4,300,678 | 11/1981 | Gyure et al. . |
| 4,375,849 | 3/1983 | Hanifl . |
| 4,430,082 | 2/1984 | Schwabacher . |
| 4,592,744 | 6/1986 | Jagger et al. . |
| 4,634,428 | 1/1987 | Cuu . |
| 4,643,722 | 2/1987 | Smith, Jr. . |
| 4,659,330 | 4/1987 | Nelson et al. . |
| 4,664,259 | 5/1987 | Landis . |
| 4,664,654 | 5/1987 | Strauss . |
| 4,681,567 | 7/1987 | Masters et al. . |
| 4,695,274 | 9/1987 | Fox . |
| 4,702,738 | 10/1987 | Spencer . |
| 4,723,943 | 2/1988 | Spencer . |
| 4,728,320 | 3/1988 | Chen . |
| 4,728,321 | 3/1988 | Chen . |
| 4,731,059 | 3/1988 | Wanderer et al. . |
| 4,735,311 | 4/1988 | Lowe et al. . |
| 4,735,618 | 4/1988 | Hagen . |
| 4,737,144 | 4/1988 | Choksi . |
| 4,738,663 | 4/1988 | Bogan . |
| 4,743,233 | 5/1988 | Schneider . |
| 4,747,836 | 5/1988 | Luther . |
| 4,772,272 | 9/1988 | McFarland . |
| 4,778,453 | 10/1988 | Lopez . |
| 4,781,697 | 11/1988 | Slaughter . |

(List continued on next page.)

FOREIGN PATENT DOCUMENTS

| | | |
|---|---|---|
| WO 87/07162 | 12/1987 | PCT Int'l Appl. . |
| 9001348 | 2/1990 | PCT Int'l Appl. ................. 604/192 |
| WO 91/09637 | 7/1991 | PCT Int'l Appl. . |
| WO 91/09638 | 7/1991 | PCT Int'l Appl. . |
| WO 91/09639 | 7/1991 | PCT Int'l Appl. . |
| 1233302 | 5/1971 | United Kingdom . |
| 2240273 | 3/1991 | United Kingdom . |
| 2239604 | 7/1991 | United Kingdom . |
| 2239607 | 7/1991 | United Kingdom . |
| 2240477 | 8/1991 | United Kingdom . |

*Primary Examiner*—William I. Price
*Attorney, Agent, or Firm*—Pollock, Vande Sande & Priddy

[57] ABSTRACT

The needle assembly holder of the present invention has mounted about its receptacle end a rotatable safety sheath so that irrespective of how the top of the cannula of the needle assembly is oriented with respect to the holder, the user can nonetheless obtain an unobstructed view of the tip of the cannula by rotating the safety sheath out of her line of sight.

14 Claims, 5 Drawing Sheets

U.S. PATENT DOCUMENTS

| | | |
|---|---|---|
| 4,782,841 | 11/1988 | Lopez . |
| 4,790,828 | 12/1988 | Dombrowski et al. . |
| 4,795,432 | 1/1989 | Karczmer . |
| 4,795,443 | 1/1989 | Permenter et al. . |
| 4,801,295 | 1/1989 | Spencer . |
| 4,804,372 | 2/1989 | Laico et al. . |
| 4,813,426 | 3/1989 | Haber et al. . |
| 4,816,022 | 3/1989 | Poncy . |
| 4,816,024 | 3/1989 | Sitar et al. . |
| 4,819,659 | 4/1989 | Sitar . |
| 4,820,277 | 4/1989 | Norelli . |
| 4,826,490 | 5/1989 | Byrne et al. . |
| 4,826,491 | 5/1989 | Schramm . |
| 4,838,871 | 6/1989 | Luther . |
| 4,842,587 | 6/1989 | Poncy . |
| 4,846,796 | 7/1989 | Carrell et al. . |
| 4,850,968 | 7/1989 | Romano . |
| 4,850,976 | 7/1989 | Heinrich et al. . |
| 4,850,977 | 7/1989 | Bayless . |
| 4,850,978 | 7/1989 | Dudar et al. . |
| 4,850,994 | 7/1989 | Zerbst et al. . |
| 4,850,996 | 7/1989 | Cree . |
| 4,858,607 | 8/1989 | Jordan et al. . |
| 4,863,434 | 9/1989 | Bayless . |
| 4,863,435 | 9/1989 | Sturman et al. . |
| 4,863,436 | 9/1989 | Glick . |
| 4,867,746 | 9/1989 | Dufresne . |
| 4,872,552 | 10/1989 | Unger . |
| 4,874,383 | 10/1989 | McNaugton . |
| 4,874,384 | 10/1989 | Nunez . |
| 4,883,469 | 11/1989 | Glazier . |
| 4,886,503 | 12/1989 | Miller . |
| 4,888,001 | 12/1989 | Schoenberg . |
| 4,892,107 | 1/1990 | Haber . |
| 4,892,521 | 1/1990 | Laico et al. . |
| 4,900,309 | 2/1990 | Netherton et al. . |
| 4,927,019 | 5/1990 | Haber et al. ............... 206/365 |
| 4,944,397 | 7/1990 | Miller ........................ 206/365 |
| 4,982,842 | 1/1991 | Hollister .................... 206/365 |

NEEDLE ASSEMBLY HOLDER WITH ROTATABLE SAFETY SHEATH MEMBER

FIELD OF THE INVENTION

This invention relates to application Ser. No. 663,454, entitled "Needle Protection Device", filed Mar. 4, 1991 by the same inventor and assigned to the same assignee as the instant invention. The disclosure of the '454 application is hereby incorporated to this application by reference. This invention is further related to application Ser. No. 561,459, entitled "Safety Needle Container", filed Aug. 1, 1990 by the same inventor and assigned to the same assignee as the instant invention. The disclosure of the '459 application is also hereby incorporated to this application by reference.

In particular, the present invention relates to a needle protection device to be used with a fluid holding tube which is adaptable to prevent a user, or a bystander, from being accidentally pricked by the sharp end of a contaminated needle.

BACKGROUND OF THE INVENTION

In the '454 application, a double-ended needle assembly holder, used in conjunction with an evacuated blood collection tube, is disclosed to have a housing that is pivotable to a position in substantial alignment with the longitudinal axis of the needle such that, once the housing is pivoted to the alignment position, the needle is retained therein so as to preclude the sharp end of the needle from being exposed.

The '454 safety device works well but for the fact that the user of the device, for example a phlebotomist or a nurse, is oftentimes blocked by the housing from having a clear view of the tip of the needle (cannula). To elaborate, ordinarily a phlebotomist, when obtaining fluid, as for example blood, from a patient, would position the cannula such that its bevel faces up. For this discussion, the bevel of a cannula is understood to be the sharp, butting end of the cannula. The reason that a phlebotomist wants to position the bevel of the cannula to face up is so that she can see the sharp point, rather than the round end, of the cannula so that the cannula can be more easily and accurately inserted into, for example the vein, of a patient. But since the needle assembly is threaded into the '454 safety device such that it may end up in any orientation, the safety housing attached to the '454 device would sometimes get in the way and prevent the phlebotomist from viewing the true angle of the cannula.

SUMMARY OF THE PRESENT INVENTION

To eliminate the sometimes disadvantageous aspect of the '454 device, the present invention safety device has attached to the extension of its tube holder a rotatable safety sheath member. Specifically, the holder extension has a circumferential protuberance, or boss, at its outer circumference. A safety housing, or sheath, whose base has a corresponding internal circumferential groove is mated with the holder extension such that the base is rotatable about the holder extension, via the interaction between the internal groove of the housing base and the external boss of the housing extension. With proper molding, friction between the internal groove of the base of the housing and the external boss of the holder extension can be such that the housing is not freely rotatable about the holder extension. In other words, in order to rotate the housing, a force has to be applied.

An alternative embodiment of the present invention includes the integration somewhere along the housing a crushable or collapsible section and the adaption of an elastomeric material at the cap section of the housing so that the tip of a contaminated needle can be securely sealed to provide yet an additional safety measure.

It is therefore an objective of the present invention to provide a safety device holder whose protective housing is rotatable away from the line of view of the user so that a cannula can be accurately inserted into a patient.

BRIEF DESCRIPTION OF THE DRAWINGS

The above-mentioned objective and advantages of the present invention will become more apparent and the invention itself will be best understood by reference to the following description of embodiments of the present invention taken in conjunction with the accompanying drawings, wherein.

DETAILED DESCRIPTION OF THE INVENTION

Figure 1:
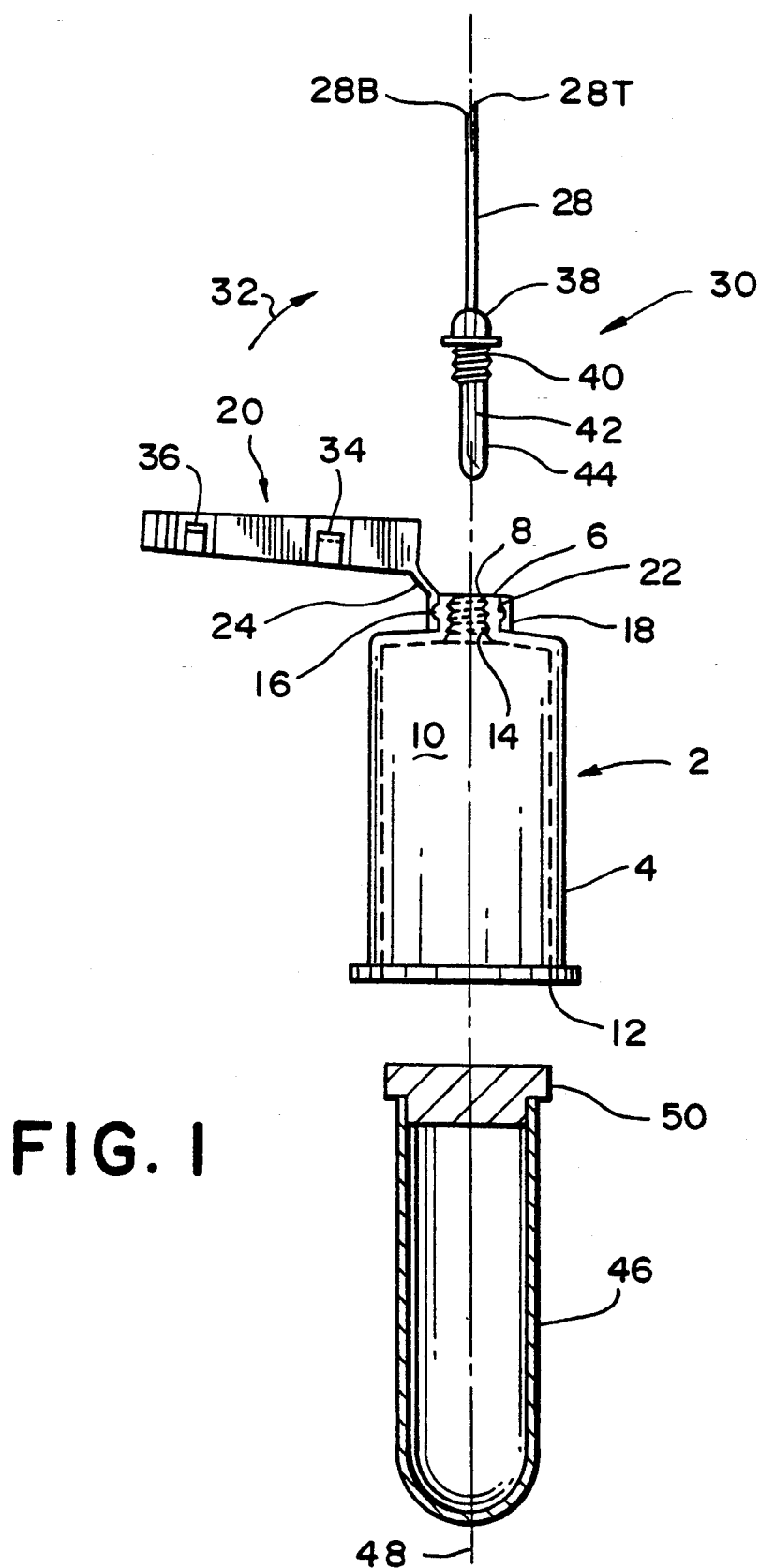
FIG. 1 is a side view of an embodiment of the present invention shown in alignment with a double-ended needle assembly and a fluid collection tube.

With reference to FIG. 1, the present invention safety device is shown to have a fluid container holder 2, otherwise known in the industry as a VACUTAINER holder, having a hollow main body section 4 and a receptacle end 6 integrally extending therefrom. An aperture extends from opening 8 of receptacle end 6 to cavity 10 of main body section 4. An opening 12 provides passage from the other end of holder 2 into cavity 10. The inner circumference of receptacle end 6 is threaded, as designated by 14.

Figure 4:
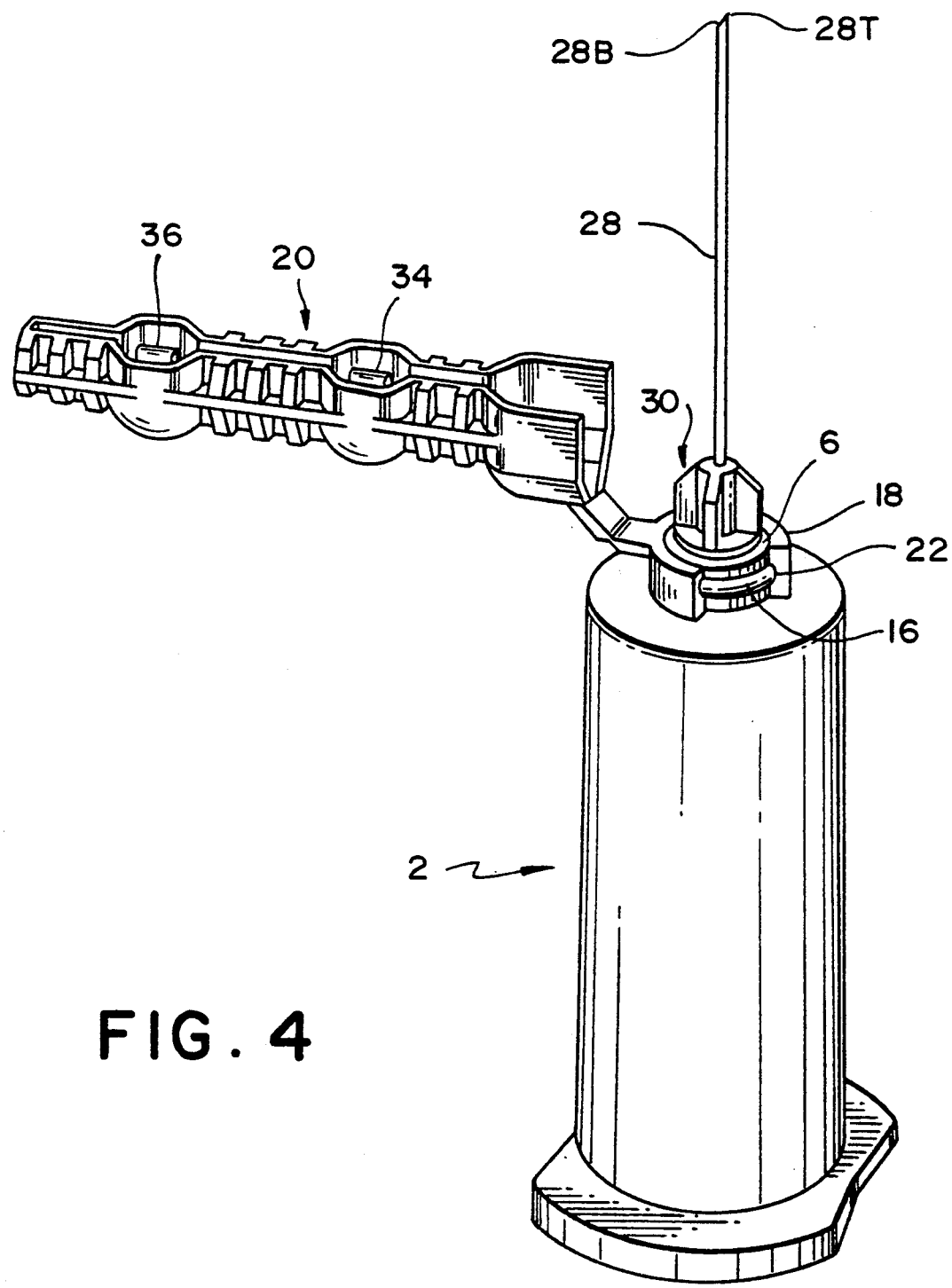
FIG. 4 is a perspective view of the safety device of the present invention having mated thereto a needle assembly.

For the present invention embodiment, formed around the outer circumference of receptacle end 6 is a circumferential protuberance, or boss, 16 about which a base 18 of a safety sheath or housing 20 is fitted, via an internal circumferential groove 22 at base 18. Base 18 is substantially formed in the shape of a non-enclosed ring, as shown in FIG. 4, and is hardpressed onto receptacle end 6 for rotatably mating its internal groove 22 to external boss 16 of receptacle end 6. The respective dimensions of boss 16 and internal groove 22, and receptacle end 6 and base 18, are such that base 18 is held frictionally against receptacle end 6 so that the former can be forced to freely rotate about the latter. In other words, in order to rotate base 18 about receptacle end 6, a sufficient moment of torque is necessary. Putting it differently, once base 18 has been rotated to a certain orientation about receptacle end 6, it will stay in that orientation until additional torque force is exerted.

Connected to base 18, via flexible hinge 24, is housing 20. The construction of housing 20 has been given in detail in the above referenced '558 and '454 applications, as well as U.S. Pat. No. 4,982,842, the disclosure of which is incorporated by reference herein. Briefly, as shown in FIG. 1, housing 20 has an elongated slot 26 (see FIG. 3) through which a needle or cannula, such as 28 of the double-ended needle assembly 30, can pass when housing 20 is pivoted toward the longitudinal axis of cannula 28 via a movement as indicated by directional arrow 32. Integrally formed within housing 20 are locking means such as, for example, hooking means (hooks) 34 and 36. The hooking means each have a finger portion that biases against cannula 28 when housing 20 is pivoted to envelop the same, but which would then return to its original position once cannula 28 has passed the same to thereby permanently retain cannula 28 within housing 20. Thus, as discussed in detail in the herein incorporated by reference '842 patent, locking means 34 and 36 in essence prevent relative movement between cannula 28 and housing 20, once housing 20 has been pivoted to envelop the same. The pivoting action of housing 20 is made possible by living hinge 24.

In operation, double-ended needle assembly 30 is connected to receptacle end 6 by turning its hub 38 so that it threadingly mates, via its threads 40, with the threaded aperture of receptacle end 6. Needle assembly 30 has, in addition to cannula 28, which is used to puncture, i.e. invasively contact a patient, an opposed cannula 42 surrounded by an elastomeric shroud 44. Once needle assembly 30 is mated with receptacle end 6, cannula 42 and shroud 44 are extended into cavity 10 of holder 2.

To allow an user a clear view of tip 28T so that cannula 28 can be more accurately inserted into the vein of a patient, for the present invention safety device, holder 2 can be reoriented such that bevel 28B is oriented to face up. And if housing 20 obstructs the view of the user from bevel 28B of cannula 28, it is rotated away by applying a torque movement thereagainst so that base 18 rotates about receptacle end 6. Cannula 28 can therefore be clearly observed, as it is being inserted into the patient. Thereafter, a fluid container tube, such as 46, is inserted along longitudinal axis 48 through opening 12 into cavity 10 of holder 2. As tube 46 is pushed thereagainst, shroud 44 is pushed upwards so that the tip of cannula 42 would penetrate through elastomeric gasket 50 to effect fluid communication, via cannulas 28 and 42, between the patient and tube 46.

Once the necessary fluid, as for example blood, is withdrawn, tube 46 is removed from cavity 10. Thereafter, cannula 28 is removed from the patient. To ensure that the thus contaminated cannula 28 is not exposed and that no one is accidentally pricked thereby, by a single handed operation, as for example pushing the end portion of housing against some immobile object, housing 20 is pivoted toward longitudinal axis 48 to envelop cannula 28 so that either one, or both, of hooks 34 and 36 would securely retain cannula 28 within housing 20. The thus used holder 2, along with the permanently retained needle assembly 30, may be disposed of in a safe manner as a single unit.

Figure 2:
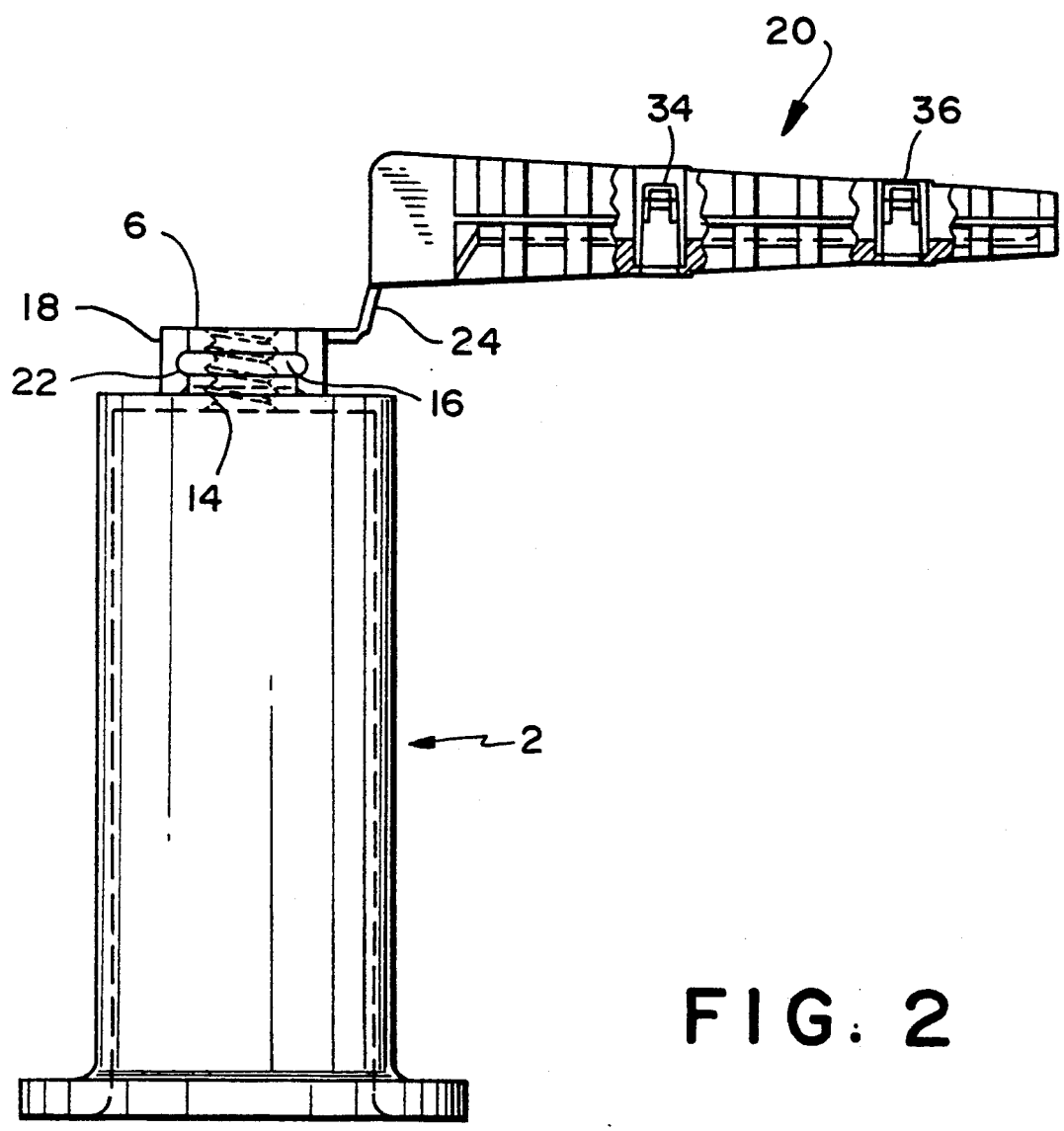
FIG. 2 is a semi-cutaway side view of the safety device of the present invention.
Figure 3:
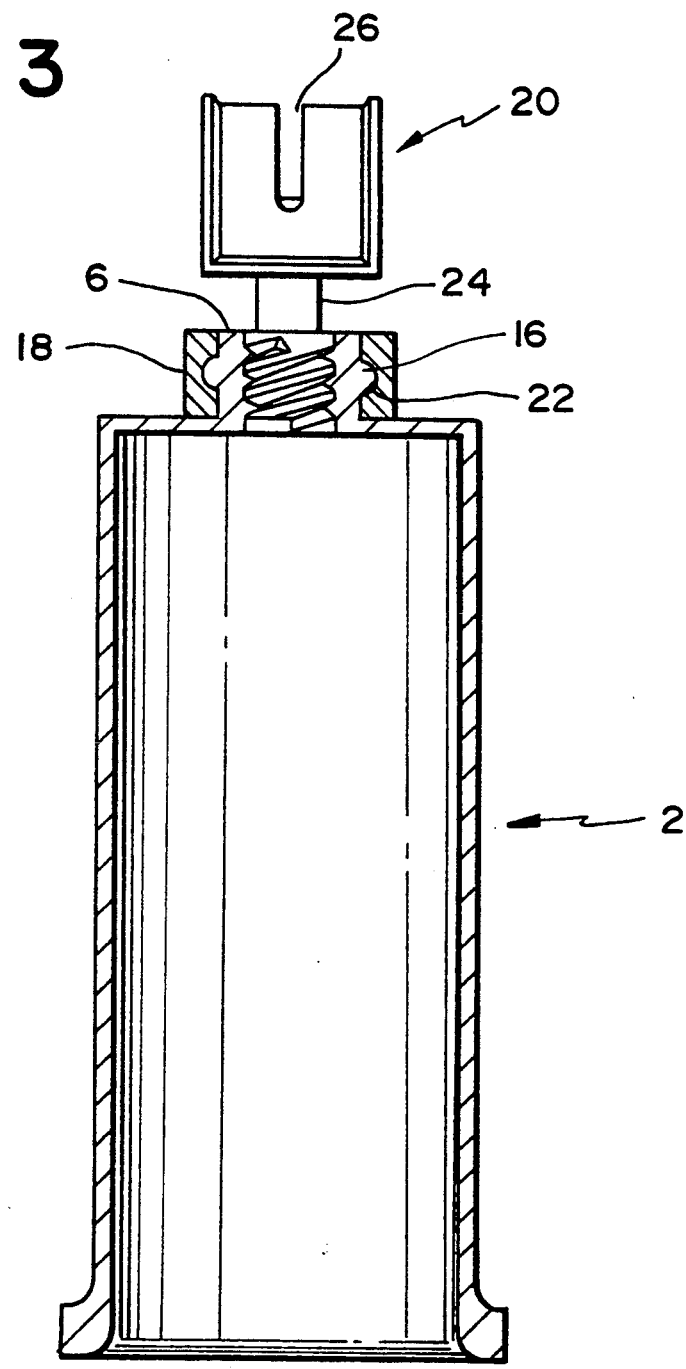
FIG. 3 is a cutaway front view of the safety device of the present invention.

FIGS. 2 and 3 show with greater detail and clarity tube holder 2 and the interaction thereof with housing 20 via the rotation of base 18 about receptacle end 6. The interaction between internal groove 22 of base 18 and circumferential boss 16 of receptacle end 6 is also more clearly illustrated in FIGS. 2 and 3.

FIG. 4 shows a perspective view of the present invention safety device having mated to its receptacle end 6 needle assembly 30. As shown, base 18 of housing 20 is not fully enclosed but rather is opened at one end so that it can be press fitted to receptacle end 6. As should readily be appreciated, base 18 can be formed with the requisite material (for example plastic) and dimension such that once it fittingly mates with receptacle end 6, it cannot be easily removed therefrom. Furthermore the respective dimensions of base 18 and receptacle end 6, more specifically that of internal groove 22 and external boss 16, are such that the friction existing between the parts prevents base 18 of housing 20 from freely rotating about receptacle end 6. Thus, once housing 20 is moved to a given orientation, it stays in that orientation until it is further moved by a torque movement.

Figure 5:
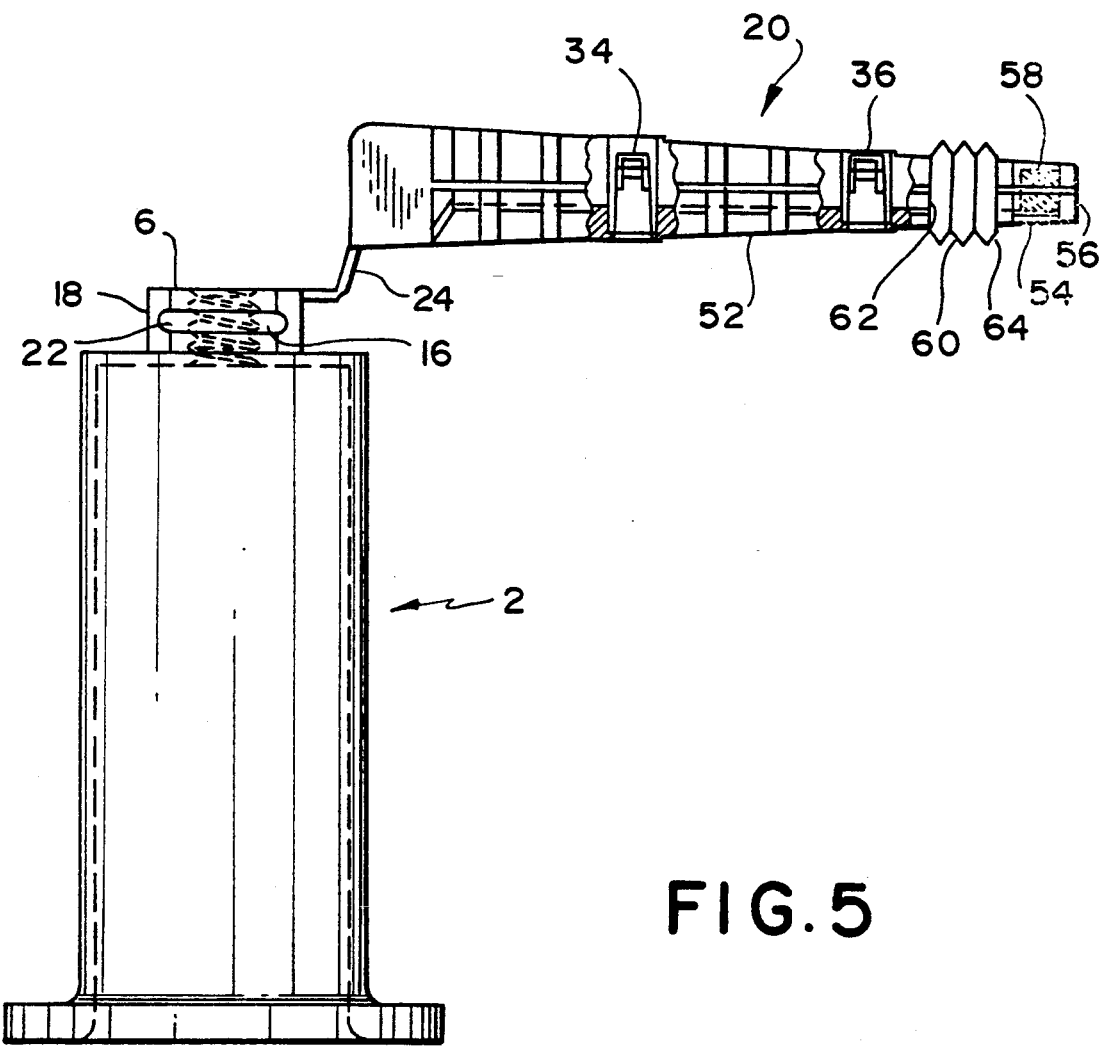
FIG. 5 is a semi-cutaway view of another embodiment of the present invention safety device.

FIG. 5 illustrates a second embodiment of the present invention. Elements that are the same as those of the previously discussed embodiment or perform the same functions are labelled the same. The FIG. 5 embodiment likewise has a base 18 which is rotatable about receptacle end 6 of holder 2, by means of the interaction between respective internal groove 22 and circumferential boss 16. For the FIG. 5 embodiment, however, housing 20 has a collapsible or crushable section 60 sandwiched between and integrally connecting a main body section 52 and a cap section 54. Adapted to cap section 54 is an elastomeric material 58 into which the tip of a contaminated cannula would penetrate—after housing 20 has been pivoted to envelop the cannula so that the same is securely retained by hooking means 34 and 36, and end 56 of housing 20 pushed longitudinally against an immobile object to effect a relative movement urging main body section 52 and cap section 54 toward each other to collapse crushable section 60. A more in depth discussion of the crushable section is given in the above incorporated by reference '459 application.

Inasmuch as the present invention is subject to many variations, modifications and changes in detail, it is intended that all matter described throughout this specification and shown in the accompanying drawings be interpreted as illustrative only and not in a limiting sense. Accordingly, it is intended that the invention be limited only by the spirit and scope of the hereto appended claims.

I claim:

1. A safety device to be used with a needle assembly having a first end for invasively contacting a body and a second end for communicating with a container, comprising:

a holder having a hollow main body section and a receptacle end extending therefrom, said holder further having an open end through which at least a portion of said container is inserted into said main body section, said receptacle end of said holder being mated with said needle assembly such that at least a portion of said second end extends into said main body section to be in fluid communication with said inserted portion of said container to provide a conduit to pass fluid between said body and said container;

housing means having a base portion rotatably connected about said receptacle end of said holder, and a body portion extending from said base portion and pivotable toward a position in substantial alignment along the longitudinal axis of said needle assembly, said body portion being rotatable about said needle assembly via said base portion and including locking means for substantially fixedly retaining said first end of said needle assembly within said body portion once said body portion has been pivoted to said alignment position to envelop said first end of said needle assembly.

2. The safety device of claim 1, wherein said receptacle end has extending therearound at its outer circumference a circumferential boss about at least a portion of which a corresponding internal circumferential groove of said base portion is rotatably mated to.

3. The safety device of claim 1, wherein said body portion of said housing means comprises a longitudinal sheath having an elongated slot through which said first end of said needle assembly passes when said sheath is pivoted to said alignment position.

4. The safety device of claim 1, wherein said locking means comprises at least one hooking means integral of said body portion of said housing means to prevent relative movement between said first end of said needle assembly and said body portion once said body portion is pivoted to said alignment position.

5. The safety device of claim 1, wherein said body portion is integrally connected to said base portion by a flexible hinge means.

6. The safety device of claim 1, wherein said container comprises a fluid collection tube into which fluid from said body is collected.

7. The safety device of claim 1, wherein said needle assembly comprises a hub; and
wherein said receptacle end of said holder is internally threaded for threadedly mating with said hub of said needle assembly.

8. The safety device of claim 1, wherein said body portion of said housing means includes at least a cap portion and a main portion flexibly connected to said base portion, further comprising:
a collapsible section interposed between and integrally connecting said cap and main portions; and
means adapted to said cap portion to substantially sealingly secure the tip of said first end of said needle assembly after said body portion has been pivoted to said alignment position and said cap and main portions relatively urged toward each other to collapse said collapsible section.

9. A safety device for a double-ended needle assembly having opposed cannula portions, comprising:
a holder having a hollow main body section and a receptacle end extending therefrom, said holder further having an open end through which at least a portion of a container is insertable into said main body section, said receptacle end of said holder being mated with said needle assembly such that at least a portion of one of said opposed cannula portions of said needle assembly extends into said main body section to be in communication with said insertable portion of said container;
housing means flexibly connected to and rotatable about at least a portion of said receptacle end of said holder, said housing means rotatable about said needle assembly so as not to obstruct the view of an operator of the other of said opposed cannula portions, said housing means further pivotable toward a position in substantial alignment along the longitudinal axis of said needle assembly for enveloping said other of said opposed cannula portions, said housing means including locking means for substantially fixedly retaining said other of said opposed cannula portions within said housing means once said housing means is pivoted to said alignment position.

10. The safety device of claim 9, wherein said receptacle end has extending around its outer circumference a circumferential boss about at least a portion of which a corresponding internal circumferential groove of a base section of said housing means is rotatably mated to.

11. The safety device of claim 9, wherein said housing means comprises a longitudinal sheath having an elongated slot through which said other of said opposed cannula portions passes when said sheath is pivoted to said position.

12. The safety device of claim 9, wherein said locking means comprises at least one hooking means integral of said housing means for preventing relative movement between said other of said opposed cannula portions and said housing means.

13. The safety device of claim 10, wherein said housing means comprises a body section, and wherein said body section is integrally connected to said base section via a flexible hinge means.

14. The safety device of claim 10, wherein said body portion of said housing means includes at least a cap section and a main section, further comprising:
a collapsible section integrally interposed between and connecting said cap and main sections; and
means adapted to said cap section of said housing means to substantially sealingly secure the tip of said other of said opposed cannula portions after said housing means has been pivoted to said substantial alignment position and said cap and main sections relatively urged toward each other to compress said collapsible section.

* * * * *